(12) United States Patent
Carranza et al.

(10) Patent No.: US 8,779,121 B2
(45) Date of Patent: Jul. 15, 2014

(54) PROCESS FOR THE SYNTHESIS OF 3-(2-BROMO-4,5-DIMETHOXYPHENYL) PROPANENITRILE, AND APPLICATION IN THE SYNTHESIS OF IVABRADINE AND ADDITION SALTS THEREOF WITH A PHARMACEUTICALLY ACCEPTABLE ACID

(71) Applicant: Les Laboratoires Servier, Suresnes Cedex (FR)

(72) Inventors: Maria Del Pilar Carranza, Villarrubia DeLos Ojos (ES); Maria Isabel Garcia Aranda, Toledo (ES); José Lorenzo Gonzalez, Toledo (ES); Frédéric Sanchez, Cobisa (ES)

(73) Assignee: Les Laboratoires Servier, Suresnes Cedex (FR)

( * ) Notice: Subject to any disclaimer, the term of this patent is extended or adjusted under 35 U.S.C. 154(b) by 0 days.

(21) Appl. No.: 14/051,805

(22) Filed: Oct. 11, 2013

(65) Prior Publication Data

US 2014/0107334 A1    Apr. 17, 2014

(30) Foreign Application Priority Data

Oct. 12, 2012  (FR) ...................... 12 59745

(51) Int. Cl.
*C07D 223/14* (2006.01)
*C07C 249/00* (2006.01)
*C07C 251/00* (2006.01)

(52) U.S. Cl.
USPC .......................................... 540/523; 558/410

(58) Field of Classification Search
USPC .......................................... 540/523; 558/410
See application file for complete search history.

(56) References Cited

U.S. PATENT DOCUMENTS 4,618,683 A    10/1986   DeBernardis et al.

FOREIGN PATENT DOCUMENTS

| DE | 2303919 | 8/1973 |
| WO | WO 2011/008597 | 1/2011 |
| WO | WO 2011/138625 | 11/2011 |

OTHER PUBLICATIONS

Paull K.D., et al., Journal of Organic Chemistry, vol. 37, No. 21, pp. 3374-3376, Jan. 1, 1972.
Preliminary Search Report for FR 1200745 of Jul. 3, 2013.
S.D. Sanders. et al., "Supplementary Material for Chemical Communicaiton", The Royal Society of Chemistry 2009, Jan. 1, 2009, pp. S1-S20.
Shanina D. Sanders, et at Chemical Communications. No. 34, pp. 5135-3157. Jan. 1, 2009.
Zhao Sheng Yin, et al., Journal of Chemical Research, No. 7, pp. 420-422, Jan. 1, 2009.

*Primary Examiner* — Bruck Kifle
(74) *Attorney, Agent, or Firm* — Hueschen and Sage

(57) ABSTRACT

Process for the synthesis of the compound of formula (I):

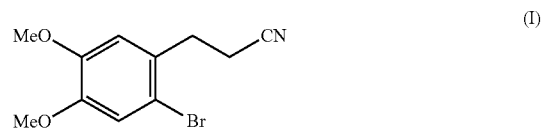

Application in the synthesis of ivabradine, addition salts thereof with a pharmaceutically acceptable acid and hydrates thereof.

18 Claims, No Drawings

PROCESS FOR THE SYNTHESIS OF 3-(2-BROMO-4,5-DIMETHOXYPHENYL)PROPANENITRILE, AND APPLICATION IN THE SYNTHESIS OF IVABRADINE AND ADDITION SALTS THEREOF WITH A PHARMACEUTICALLY ACCEPTABLE ACID

The present invention relates to a process for the synthesis of (3-(2-bromo-4,5-dimethoxyphenyl)propanenitrile of formula (I):

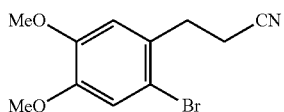

(I)

and to the application thereof in the synthesis of ivabradine and addition salts thereof with a pharmaceutically acceptable acid.

The compound of formula (I) obtained in accordance with the process of the invention is useful in the synthesis of ivabradine of formula (II):

(II)

or 3-{3-[{[(7S)-3,4-dimethoxybicyclo[4.2.0]octa-1,3,5-trien-7-yl]methyl}(methyl)amino]-propyl}-7,8-dimethoxy-1,3,4,5-tetrahydro-2H-3-benzazepin-2-one, which may be converted into an addition salt thereof with a pharmaceutically acceptable acid selected from hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid and camphoric acid, and into hydrates thereof.

Ivabradine, and its addition salts with a pharmaceutically acceptable acid, and more especially its hydrochloride, have very valuable pharmacological and therapeutic properties, especially bradycardic properties, making those compounds useful in the treatment or prevention of various clinical situations of myocardial ischaemia such as angina pectoris, myocardial infarction and associated rhythm disturbances, and also in various pathologies involving rhythm disturbances, especially supraventricular rhythm disturbances, and in heart failure.

The addition salt of ivabradine with a pharmaceutically acceptable acid may be prepared starting from an acid selected from hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid and camphoric acid.

The preparation and therapeutic use of ivabradine and its addition salts with a pharmaceutically acceptable acid, and more especially its hydrochloride, have been described in the European patent specification EP 0 534 859.

That patent specification describes the preparation of ivabradine starting from 3,4-dimethoxybicyclo[4.2.0]octa-1,3,5-triene-7-carbonitrile of formula (III):

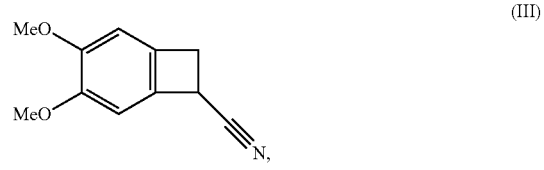 [SMILES: COc1cc2c(cc1OC)C(C#N)C2]

(III)

which is converted into the compound of formula (IV):

(IV)

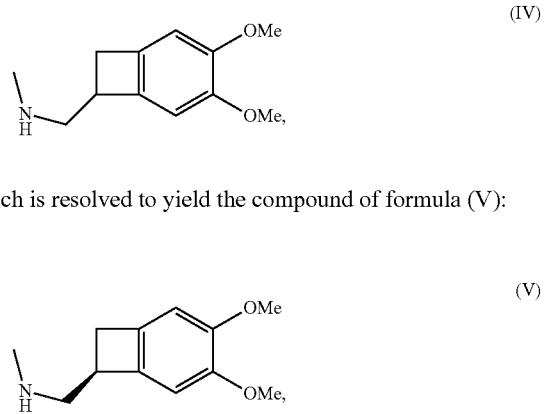

which is resolved to yield the compound of formula (V):

(V)

which is reacted with the compound of formula (VI):

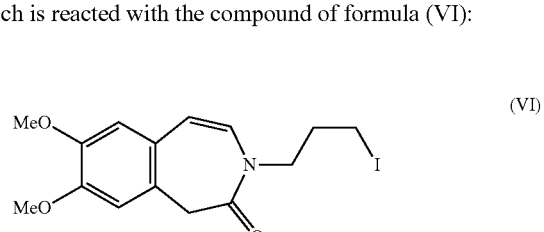

(VI)

to yield the compound of formula (VII):

(VII)

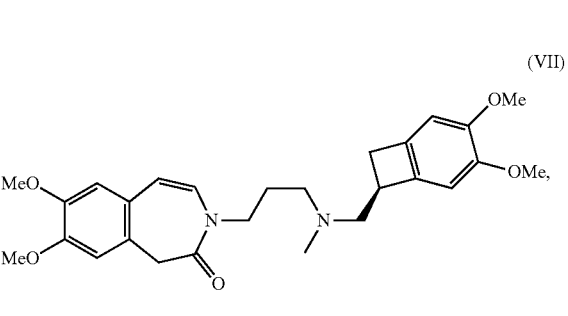 [SMILES: COc1cc2c(cc1OC)CC(=O)N(CCCN(C)C[C@H]1Cc3cc(OC)c(OC)cc31)C=C2]

the catalytic hydrogenation of which yields ivabradine, which is then converted into its hydrochloride.

The preparation of the compound of formula (III) starting from the compound of formula (I) is described in *Tetrahedron* 1973, 29, pp 73-76.

That same document also describes a synthesis route for the compound of formula (I), starting from 2-bromo-4,5-dimethoxybenzaldehyde, in three steps with an overall yield of 65%.

The preparation of the compound of formula (I) by performing a bromination reaction on 3-(3,4-dimethoxyphenyl)propanenitrile in the presence of dibromine in acetic acid is described in *J. Org. Chem* 1972, vol. 37, no. 21, pp 3374-3376, with a yield of 48%.

More recently, Zhao et al. have described synthesis of the compound of formula (I), starting from 3,4-dimethoxybenzaldehyde, in three steps in an overall yield of 51% (CN101 407 474 A and *J. Chem. Res.* 2009, 7, pp 420-422).

The compound of formula (I) is a key intermediate in the synthesis of ivabradine.

In view of the industrial value of ivabradine and its salts, it has been imperative to find an effective process allowing (3-(2-bromo-4,5-dimethoxyphenyl)propanenitrile of formula (I) to be obtained in an excellent yield.

The present invention relates to a process for the synthesis of the compound of formula (I):

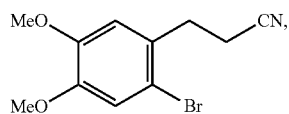

characterised in that the compound of formula (VIII):

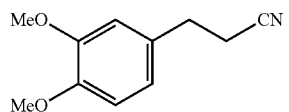

is subjected to the action of N-bromosuccinimide in the presence of an organic solvent to yield the compound of formula (I).

Among the organic solvents that may be used to carry out the conversion of the compound of formula (VIII) into the compound of formula (I), there may be mentioned, without implying any limitation, N,N-dimethylformamide, tetrahydrofuran, acetonitrile, acetic acid, methanol, dichloromethane and toluene.

The solvent preferably used to carry out the conversion of the compound of formula (VIII) into the compound of formula (I) is N,N-dimethylformamide.

The conversion of the compound of formula (VIII) into the compound of formula (I) is carried out at a temperature preferably between −10° C. and 30° C., inclusive.

The present invention relates also to a process for the synthesis of the compound of formula (I) starting from the compound of formula (VIII), characterised in that said compound of formula (VIII) is prepared starting from the compound of formula (IX):

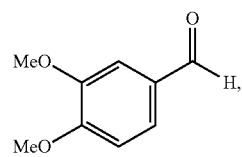

which is converted into the compound of formula (X):

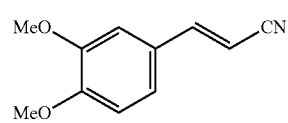

in the presence of a phosphorus ylide and a base in an organic solvent,
which is converted into the compound of formula (VIII):

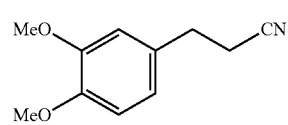

by a reduction reaction in the presence of a hydride donor agent in an organic solvent or mixture of organic solvents, which is converted into the product of formula (I):

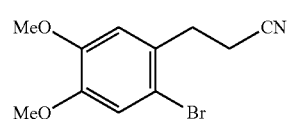

in accordance with the process described hereinabove.

Among the phosphorus ylides that may be used to carry out the conversion of the compound of formula (IX) into the compound of formula (X), there may be mentioned, without implying any limitation, diethyl cyanomethyl phosphonate and (triphenylphosphoranylidene)acetonitrile.

The phosphorus ylide preferably used to carry out the conversion of the compound of formula (IX) into the compound of formula (X) is diethyl cyanomethyl phosphonate.

Among the bases that may be used to carry out the conversion of the compound of formula (IX) into the compound of formula (X), there may be mentioned, without implying any limitation, potassium tert-butoxide, sodium hydride, triethylamine and potassium hydrogen carbonate.

The base preferably used to carry out the conversion of the compound of formula (IX) into the compound of formula (X) is potassium tert-butoxide.

Among the organic solvents that may be used to carry out the conversion of the compound of formula (IX) into the compound of formula (X), there may be mentioned, without implying any limitation, tetrahydrofuran, acetonitrile and toluene.

The organic solvent preferably used to carry out the conversion of the compound of formula (IX) into the compound of formula (X) is tetrahydrofuran.

The conversion of the compound of formula (IX) into the compound of formula (X) is preferably carried out at a temperature between −5° C. and 120° C., inclusive.

Among the hydride donor agents that may be used to carry the conversion of the compound of formula (X) into the compound of formula (VIII), there may be mentioned, without implying any limitation, sodium borohydride, ammonium formate in the presence of Pd/C, and formic acid in the presence of $Pd(OAc)_2$.

The hydride donor agent preferably used to carry out the conversion of the compound of formula (X) into the compound of formula (VIII) is sodium borohydride.

Among the organic solvents that may be used to carry out the conversion of the compound of formula (X) into the compound of formula (VIII), there may be mentioned, without implying any limitation, alcoholic solvents, such as methanol and ethanol, and tetrahydrofuran.

A mixture of organic solvents, preferably the mixture pyridine/methanol, may also be used to carry out the conversion of the compound of formula (X) into the compound of formula (VIII).

The conversion of the compound of formula (X) into the compound of formula (VIII) is preferably carried out at a temperature between 25° C. and 110° C., inclusive.

The present invention relates also to a process for the synthesis of ivabradine starting from the compound of formula (I) prepared in accordance with the process of the invention and converted into the compound of formula (III) following the teaching of the prior art (*Tetrahedron* 1973, 29, pp 73-76) by an intramolecular cyclisation reaction in a basic medium, said compound of formula (III) then being converted into ivabradine in accordance with the process described in EP 0 534 859.

The Examples that follow illustrate the invention.

The melting points were measured using a BÜCHI B-545 Melting Point Apparatus (Volt. 230 VAC, Freq. 50/60 Hz, Power max. 220 W).

List of Abbreviations Used

DMF: N,N-dimethylformamide
HPLC: High Performance Liquid Chromatography
NBS: N-bromosuccinimide
m.p.: melting point
THF: tetrahydrofuran Preparation A:
(2E)-3-(3,4-dimethoxyphenyl)prop-2-enenitrile 7 g of 3,4-dimethoxybenzaldehyde (42.1 mmoles) are dissolved in 84 mL of THF and the solution is cooled to 0° C. 8.2 g of diethyl cyanomethyl phosphonate (7.5 mL, 46.3 mmoles, 1.1 eq.) and subsequently 5.2 g of potassium tert-butoxide (46.3 mmoles, 1.1 eq.) are added little by little. The mixture is stirred for one hour at 0° C. and then overnight at ambient temperature. The reaction mixture is hydrolysed using 175 mL of water and extracted twice with dichloromethane. The organic phases are collected and the solvent is evaporated off under reduced pressure to yield 7.69 g of the title product in the form of a beige solid.
Yield=96.5%
m.p.=93-98° C.

Preparation B:
3-(3,4-dimethoxyphenyl)propanenitrile

To a solution of 1 g (5.3 mmoles) of (2E)-3-(3,4-dimethoxyphenyl)prop-2-enenitrile in 9.3 mL of pyridine and 2.8 mL of methanol there is added, little by little, 0.24 g of $NaBH_4$ (6.3 mmol, 1.2 eq.). The reaction mixture is heated at reflux (100° C.) for 9 hours. After cooling to ambient temperature, the reaction mixture is added to a solution of 9 mL of hydrochloric acid 37% in 24 g of ice. The solution is extracted twice with dichloromethane. The organic phases are collected and the solvent is evaporated off under reduced pressure to yield 0.82 g of a red-brown oil which crystallises.
Yield=82%
m.p.=45-48° C.

EXAMPLE 1

3-(2-bromo-4,5-dimethoxyphenyl)propanenitrile

A solution of 1 g (5.3 mmoles) of 3-(3,4-dimethoxyphenyl)propanenitrile in 42 mL of DMF is cooled to 0° C. To the resulting solution there is added, little by little, 0.93 g of NBS (5.2 mmoles, 1 eq.). After stirring for 30 minutes at 0° C., the reaction mixture is brought back to ambient temperature and stirred for two hours. It is then hydrolysed using 170 mL of water and extracted twice with 130 mL of ethyl acetate. The organic phases are collected and then washed, first with saturated aqueous $Na_2S_2O_5$ solution and then with water. After evaporating off the solvent under reduced pressure, 1.29 g of a colourless oil which crystallises into a white solid are obtained.
Yield=98%
Purity (HPLC): 96.8%
m.p.=78-80° C.

EXAMPLE 2

3,4-dimethoxybicyclo[4.2.0]octa-1,3,5-triene-7-carbonitrile

Based on *Tetrahedron* 1973, 29, pp 73-76
To a solution of $NaNH_2$, prepared starting from 200 mL of liquid $NH_3$ and 1 g of Na (catalyst: $FeCl_3$) there are added, in portions, 5.4 g of 3-(2-bromo-4,5-dimethoxyphenyl)propanenitrile and the reaction mixture is stirred at ambient temperature for 2 hours. After evaporating off the excess $NH_3$, 2 g of $NH_4Cl$ and 200 mL of water are added in portions. The grey crystals formed are collected and recrystallised from ethanol to yield 2.38 g of the expected product.
Yield=74%
m.p.=84-85° C.

EXAMPLE 3

3,4-dimethoxy-N-methylbicyclo[4.2.0]octa-1,3,5-trien-7-amine

Based on EP 0 534 859

Step 1: 3,4-dimethoxybicyclo[4.2.0]octa-1,3,5-trien-7-amine hydrochloride 312 mL of a molar solution of borane complexed with THF are added dropwise, and whilst stirring at ambient temperature, to a solution of 25 g of 3,4-dimethoxybicyclo[4.2.0]octa-1,3,5-triene-7-carbonitrile in 250 mL of THF and left in contact for 12 hours; 200 mL of ethanol are then added and stirring is carried out for 1 hour. 100 mL of 3.3N ethereal HCl are added dropwise. 27.7 g of the expected product are obtained.

Yield=90% m.p.=205° C.

Step 2: ethyl (3,4-dimethoxybicyclo[4.2.0]octa-1,3,
5-trien-7-yl)carbamate 1.5 mL of ethyl chloroformate are poured into a suspension of 3.4 g of the compound obtained in Step 1 in 4.5 mL of triethylamine and 50 mL of dichloromethane and left overnight, whilst stirring at ambient temperature; washing with water and with 1N hydrochloric acid is then carried out. Drying is carried out and the solvent is evaporated off to dryness. 3.2 g of an oil corresponding to the expected product are obtained.

Yield=80%

Step 3: 3,4-dimethoxy-N-methylbicyclo[4.2.0]octa-
1,3,5-trien-7-amine 3.2 g of the compound obtained in Step 2 dissolved in 30 mL of THF are added to a suspension of 0.9 g of LiAlH$_4$ in 20 mL of THF. Refluxing is carried out for 1 hour 30 minutes, then hydrolysing using 0.6 ml of water and 0.5 mL of 20% sodium hydroxide solution and, finally, 2.3 mL of water. The mineral salts are then filtered off, rinsed with THF and then the filtrate obtained is evaporated to dryness. 2.3 g of the expected compound are obtained.

Yield=92%

EXAMPLE 4

(7S)-3,4-dimethoxy-N-methylbicyclo[4.2.0]octa-1,3,
5-trien-7-amine

Based on EP 0 534 859

The amine obtained in Example 3 is reacted with an equimolar amount of (d) camphorsulphonic acid in ethanol. After evaporating off the solvent in vacuo, the salt is recrystallised first from ethyl acetate and then from acetonitrile until the target enantiomer is obtained with an optical purity of more than 99% (evaluated by HPLC on a Chiralcel® OD column).

EXAMPLE 5

3-{3-[{[(7S)-3,4-dimethoxybicyclo[4.2.0]octa-1,3,5-
trien-7-yl]methyl}-(methyl)amino]propyl}-7,8-
dimethoxy-1,3-dihydro-2H-3-benzazepin-2-one Based on EP 0 534 859

A solution of the (d) camphorsulphonate salt obtained in Example 4 in ethyl acetate is brought to basic pH using sodium hydroxide and then the organic phase is separated off, washed, dried over Na$_2$SO$_4$ and evaporated.

A mixture composed of 5.6 g of potassium carbonate, 2.2 g of the above amine in 100 mL of acetone and 4 g of 3-(3-iodopropyl)-7,8-dimethoxy-1,3-dihydro-2H-3-benzazepin-2-one is then refluxed for 18 hours.

The solvent is evaporated off in vacuo, and the residue is taken up in ethyl acetate and then extracted with 3N hydrochloric acid.

The aqueous phase separated off is brought to basic pH using sodium hydroxide and is then extracted with ethyl acetate. After washing until neutral and drying over MgSO$_4$, evaporation in vacuo is carried out to obtain 4.5 g of an oil which is purified on a silica column using a mixture of dichloromethane/methanol (90/10) as eluant.

Yield=64%

EXAMPLE 6

3-{3-[{[(7S)-3,4-dimethoxybicyclo[4.2.0]octa-1,3,5-
trien-7-yl]methyl}-(methyl)amino]propyl}-7,8-
dimethoxy-1,3,4,5-tetrahydro-2H-3-benzazepin-2-
one Based on EP 0 534 859

5 g of the compound obtained in Example 5 in 50 mL of glacial acetic acid are hydrogenated in a Parr apparatus under a hydrogen pressure of 4.9 bar at ambient temperature for 24 hours in the presence of 1 g of palladium hydroxide 10%. The catalyst is filtered off, the solvent is evaporated off, and then the dry residue is taken up in water and ethyl acetate. The organic phase is dried over anhydrous magnesium sulphate, concentration in vacuo is carried out and then the residue is purified on a silica column using a mixture of dichloromethane/methanol (95/5) as eluant. After recrystallisation from ethyl acetate, 2 g of the expected compound are obtained.

Yield=40% m.p.=101-103° C.

The invention claimed is:

1. A process for the synthesis of a compound of formula (I):

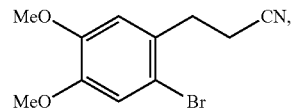 [SMILES: COc1cc(Br)c(CCC#N)cc1OC]

wherein a compound of formula (VIII):

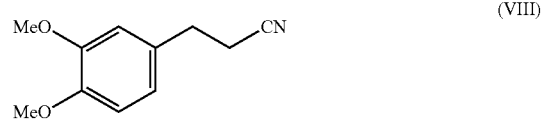 [SMILES: COc1ccc(CCC#N)cc1OC]

is subjected to the action of N-bromosuccinimide in the presence of an organic solvent to yield the compound of formula (I).

2. The process according to claim 1, wherein the organic solvent used to carry out the conversion of the compound of formula (VIII) into the compound of formula (I) is selected from N,N-dimethylformamide, tetrahydrofuran, acetonitrile, acetic acid, methanol, dichloromethane and toluene.

3. The process according to claim 2, wherein the organic solvent used to carry out the conversion of the compound of formula (VIII) into the compound of formula (I) is N,N-dimethylformamide.

4. The process according to claim 1, wherein the conversion of the compound of formula (VIII) into the compound of formula (I) is carried out at a temperature between −10° C. and 30° C., inclusive.

5. The process according to claim 1, wherein the compound of formula (VIII) is prepared starting from the compound of formula (IX):

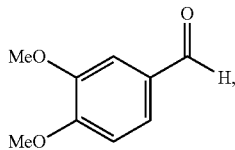

which is converted into a compound of formula (X):

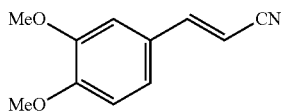

in the presence of a phosphorus ylide and a base in an organic solvent, which compound of formula (X) is converted into the compound of formula (VIII)

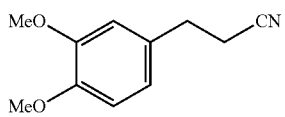

by a reduction reaction in the presence of a hydride donor agent in an organic solvent or mixture of organic solvents.

6. The process according to claim 5, wherein the phosphorus ylide used to carry out the conversion of the compound of formula (IX) into the compound of formula (X) is diethyl cyanomethyl phosphonate or (triphenylphosphoranylidene) acetonitrile.

7. The process according to claim 6, wherein the phosphorus ylide used to carry out the conversion of the compound of formula (IX) into the compound of formula (X) is diethyl cyanomethyl phosphonate.

8. The process according to claim 5, wherein the base used to carry out the conversion of the compound of formula (IX) into the compound of formula (X) is selected from potassium tert-butoxide, sodium hydride, triethylamine and potassium hydrogen carbonate.

9. The process according to claim 8, wherein the base used to carry out the conversion of the compound of formula (IX) into the compound of formula (X) is potassium tert-butoxide.

10. The process according to claim 5, wherein the organic solvent used to carry out the conversion of the compound of formula (IX) into the compound of formula (X) is selected from tetrahydrofuran, acetonitrile and toluene.

11. The process according to claim 10, wherein the organic solvent used to carry out the conversion of the compound of formula (IX) into the compound of formula (X) is tetrahydrofuran.

12. The process according to claim 5, wherein the conversion of the compound of formula (IX) into the compound of formula (X) is carried out at a temperature between −0.5° C. and 120° C., inclusive.

13. The process according to claim 5, characterised in that the hydride donor agent used to carry out the conversion of the compound of formula (X) into the compound of formula (VIII) is selected from sodium borohydride, ammonium formate in the presence of Pd/C, and formic acid in the presence of Pd(OAc)$_2$.

14. The process according to claim 13, wherein the hydride donor agent used to carry out the conversion of the compound of formula (X) into the compound of formula (VIII) is sodium borohydride.

15. The process according to claim 5, wherein the organic solvent used to carry out the conversion of the compound of formula (X) into the compound of formula (VIII) is selected from methanol, ethanol, tetrahydrofuran and a mixture pyridine/methanol.

16. The process according to claim 15, wherein the organic solvent used to carry out the conversion of the compound of formula (X) into the compound of formula (VIII) is the mixture pyridine/methanol.

17. The process according to claim 5, wherein the conversion of the compound of formula (X) into the compound of formula (VIII) is carried out at a temperature between 25° C. and 110° C. inclusive.

18. A process for the synthesis of ivabradine, or a pharmaceutically acceptable salt thereof, wherein a compound of formula (VIII)

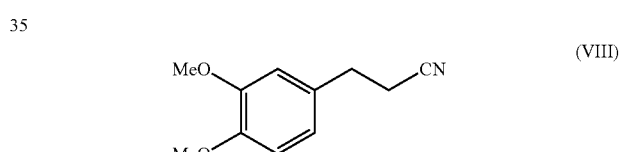

is subjected to the action of N-bromosuccinimide in the presence of an organic solvent to yield a compound of formula (I):

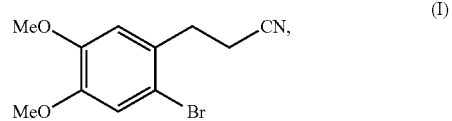 [SMILES: COc1cc(Br)c(CCC#N)cc1OC]

which compound of formula (I) is subjected to an intramolecular cyclization reaction in a basic medium to yield a compound of formula (III):

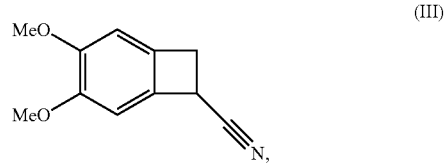 [SMILES: COc1cc2c(cc1OC)C(C#N)C2]

which compound of formula (III) is subjected to reduction conditions to yield a compound of formula (IV):

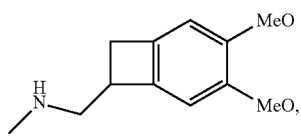

(IV)

which compound of formula (IV) is subjected to optical resolution conditions to yield a compound of formula (V):

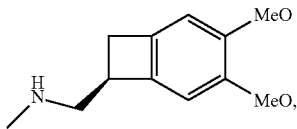

(V)

which compound of formula (V) is reacted with a compound of formula (VI):

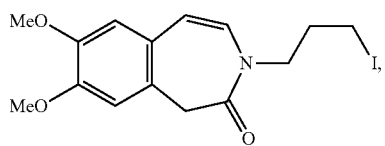

(VI)

to yield a compound of formula (VII):

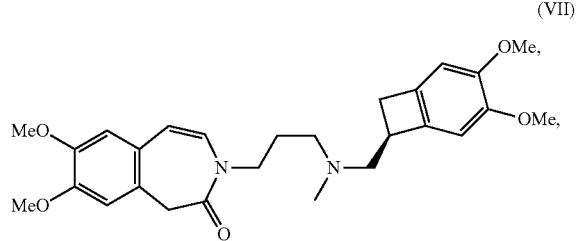 [SMILES: COc1cc2c(cc1OC)CC(=O)N(CCCN(C)C[C@H]1Cc3cc(OC)c(OC)cc31)C=C2]

(VII)

which compound of formula (VII) is subjected to catalytic hydrogenation conditions to yield ivabradine, which may optionally be converted into an addition salt thereof via treatment with a pharmaceutically acceptable acid selected from hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid and camphoric acid.

* * * * *

UNITED STATES PATENT AND TRADEMARK OFFICE
CERTIFICATE OF CORRECTION

| | | |
|---|---|---|
| PATENT NO. | : 8,779,121 B2 | Page 1 of 1 |
| APPLICATION NO. | : 14/051805 | |
| DATED | : July 15, 2014 | |
| INVENTOR(S) | : Maria Del Pilar Carranza et al. | |

It is certified that error appears in the above-identified patent and that said Letters Patent is hereby corrected as shown below:

Title Page, Other Publications, line 3: "Preliminary Search Report for FR 1200745" should be --Preliminary Search Report for FR 1259745--.

Signed and Sealed this
Fourth Day of November, 2014

Michelle K. Lee
*Deputy Director of the United States Patent and Trademark Office*